United States Patent
Prasad

(10) Patent No.: US 7,273,626 B2
(45) Date of Patent: Sep. 25, 2007

(54) HERBAL PREPARATION FOR MANAGEMENT OF CARDIOVASCULAR AND NEUROLOGIC DISORDERS

(76) Inventor: Dubey Gobind Prasad, B29/10 Nandigram, Lanka, Varanari 221005 (IN)

( * ) Notice: Subject to any disclaimer, the term of this patent is extended or adjusted under 35 U.S.C. 154(b) by 9 days.

(21) Appl. No.: 10/538,464

(22) PCT Filed: Dec. 13, 2002

(86) PCT No.: PCT/IN02/00233

§ 371 (c)(1),
(2), (4) Date: Jun. 10, 2005

(87) PCT Pub. No.: WO2004/054592

PCT Pub. Date: Jul. 1, 2004

(65) Prior Publication Data

US 2006/0034950 A1    Feb. 16, 2006

(51) Int. Cl.
*A01N 65/00*    (2006.01)

(52) U.S. Cl. .................................................... 424/725
(58) Field of Classification Search ................ None
See application file for complete search history.

(56) References Cited

U.S. PATENT DOCUMENTS

2004/0170704 A1* 9/2004 Tze et al. ................... 424/725

FOREIGN PATENT DOCUMENTS

| CN | 1113153 A | * | 6/1995 |
| JP | 08037307 | * | 1/1996 |
| WO | WO00/33659 | * | 6/2000 |

* cited by examiner

*Primary Examiner*—Christopher R. Tate
*Assistant Examiner*—Deborah A. Davis
(74) *Attorney, Agent, or Firm*—The Webb Law Firm

(57) ABSTRACT

A herbal preparation for management of cardiovascular and neurologic disorders comprising at least two of the following constituents, and preferably all three: 1. *Dioscorea bulbifera*, 2. *Hippophae rhamnoides*, 2. *Bacopa monnieri* and present in the range of: 1. *Dioscorea bulbifera* 200-500 mg, 2. *Hippophae rhamnoides* 150-400 mg, 3. *Bacopa monnieri* 100-500 mg for every 1000 mg of said preparation.

3 Claims, No Drawings

HERBAL PREPARATION FOR MANAGEMENT OF CARDIOVASCULAR AND NEUROLOGIC DISORDERS

FIELD OF INVENTION

This invention relates to a herbal preparation for management of cardiovascular and neurologic disorders and to a process for the preparation thereof.

The preparation of the present invention slows down the atherosclerolic changes and hence helpful in delaying the onset of hypertension among potential hypertension cases. The preparation also delays the development of frank diabetes mellitus and also slows down the early cognitive decline and neurologic disorders among likely patients.

The preparation is also helpful in increasing the general body resistance against physical and mental stress. It helps in neurophysiological adaption following cold stress. Such a preparation also prevents the individual from pneumonia following cold exposure.

BACKGROUND OF INVENTION

Ageing is a normal physiological phenomena resulting from intrinsic and extrinsic damage to the various organs particularly cardiovascular and neurologic system. The magnitude of ageing process depends upon genetic as well as environmental factors. A wide variety of disorders appear among the ageds.

Rapid atherosclerotic changes results in cerebrovascular accidents and ischaemic heart disease similarly due to brain ageing cognitive decline and other cognitive deficit disorders are common among the ageds. Dementia of Alzheimer's type is one of the important cause of motility and morbidity among the ageds. Dementia of Alzheimer's type is one of the important cause of motility and morbidity among the aged populations.

The currently available drugs have shown tremendous side effect and has no preventive role in age related disorders.

OBJECTS OF THE INVENTION

The main object of this preparation is to propose a novel preparation for the prevention of rapid atherosclerotic changes among the individuals showing evidence of potential hypertension.

Another object of this invention is propose a herbal preparation to delay the onset of frank diabetes.

Still another object of this invention is to propose a novel preparation for increasing general body immunity among those persons who have low body resistance.

Yet another object of this invention is to propose a novel preparation to prevent the cognitive decline among ageds.

Another object of this invention is to propose a herbal preparation to regulate abnormal lipid profile particularly LDL-c and triglycerides to prevent blockage of coronary, artery and vessels of brain.

DETAILED DESCRIPTION OF INVENTION

According to this invention there is provided a herbal preparation for management of cardiovascular and neurologic disorders comprising at least two of the following constituents, and preferably all three:
1. Dioscorea bulbifera
2. Hippophae rhamnoides
3. Bacopa monnieri and present in the range of:

| | | |
|---|---|---|
| 1. | Dioscorea bulbifera | 200-500 mg |
| 2. | Hippophae rhamnoides | 150-400 mg |
| 3. | Bacopa monnieri | 100-500 mg | for every 1000 mg of said preparation.

The preparation may also comprise known additives such as minerals, vitamin, salts, fillers (for encapsulation) and binders, if required and present in trace amounts.

| | | |
|---|---|---|
| 1. | Dioscorea bulbifera | 200-500 mg |
| 2. | Hippophae rhamnoides | 150-400 mg |
| 3. | Bacopa monnieri | 100-500 mg |

Thus, any known additive or supplement is added to prepare the final capsule if required, and present in trace amounts. Reference is made herein to a capsule. However, it would be apparent that the preparation may also be in the form of a tablet.

Preferably, the preparation comprises:

| | | |
|---|---|---|
| 1. | Dioscorea bulbifera | 200-300 mg |
| 2. | Hippophae rhamnoide | 250-350 mg |
| 3. | Bacapa monnieri | 250-5s00 mg | for every 1000 mg of the preparation.

*Dioscorea bulbifera:*

*Dioscorea bulbifera* belongs to the family of Dioscoreaceae, it is a creeping plant with a bulbous root. The plant is a climber. The tuberous bulb is about two to four inches in diameter and brown in colour. The leaves and stem of the plant contains toxic alkaloids but the tuberous pat of the plant mainly contains the terpenoidal glycosides. The remaining part of the bulb contains starch, calcium oxalate.

*Hippophae rhamnoides*

*Hippophae rhamnoides* commonly known as *Seabuckthron* is a small genus of shrubs and trees and in native of temperate region. It belongs to family elaeagnaceae. Fruits and leaves are commonly used for medicinal purpose. The fruit residue is quite rich in protein, fats, amino acids. The ripe fruits contain many type of vitamins. The stem contains 5HT the rare occurrence in the plant kingdom.

*Bacopa monnieri*

*Bacopa monnieri* is commonly known as *Brahmi* is an annual creeping plant found throughout India in wet, damp and marshy areas. In Ayurvedic medicine this plant is used as a nervine tonic in the management of mental subnormalcy, instability and epilepsy. Total plant is used for the medicine purposes. The plant contains contains crystalline compound and its one of the components crosses the blood brain barrier.

EXAMPLE 1

The preparation containing the organic extract of *Dioscorea bulbifera* was given in the dose of 100-150 mg per day did not show any action on circadian blood pressure. Similarly in this dose no alteration was observed in the level of post prandial glucose level. The effective dose varies from 200-500 mg per day. The single drug therapy significantly slow downs the process of atherosclerosis in experimental animals.

EXAMPLE 2

When the organic extract of *Dioscorea bulbifera* administered in the dose of 200-300 mg per day along with the organic-extract of fruits of *Hippophae rhamnoide* in the dose of 200-300 mg improvement was noticed in the variation of systolic and diastolic blood pressure following circadian blood pressure changes. Similarly when the organic extract of *Dioscorea bulbifera* along with *Hippophae rhamnoide* was given in the dose of 200-300 mg per day and 150 to 400 mg per day a 1 reduction in the level of systolic and diastolic blood pressure was observed following cold pressor test.

The post prandial blood glucose level also showed significant reduction in this particular range of combined effect of two drugs in relation placebo group.

EXAMPLE 3

When the organic extract of *Bacopa monnieri* in the dose of 100 mg to 200 mg per day along with the organic extract of *Hippophae rhamnoide* was administered 200-300 mg per day and *Dioscorea bulbifera* in the dose of 150-200 mg per day and a considerable improvement was noticed in general feeling of well being, better sleep and good appetite. The subjects also showed better tolerance to heat and cold. The subject developed better neurophysiological adaptation following stress.

EXAMPLE 4

When the organic extract of *Dioscorea bulbifera* was given in the dose of 200-300 mg per day along with the *Hippophae rhamnoide* in the dose of 200-350 mg per day along with the organic extract of *Bacopa monnieri* in the dose of 250-400 mg per day presented good results in the form of significant reduction in the cardiovascular reactivity and arrest the rapid decline of the cognitive function.

EXAMPLE 5

In this series when the organic extract of *Dioscorea bulbifera* in the dose of 200-300 mg per day along with organic extract of *Hippophae rhamnoide* in the dose of 250-350 mg and *Bacopa monnieri* in the dose of 250-400 mg per day was administered simultaneously twice in a day the subject reported good sleep and reduced systolic and distolic blood pressure. The cardiovascular recording was also found reduced following cold stress. About 70 percent cases reported overall feeling of well-being.

EXAMPLE 6

When the organic extract of *Hippophae rhamnoide* in the dose of 250 mg to 300 mg per day and the organic extract of *Bacopa monnieri* in the dose of 300 to 350 mg per day the individuals showed a better tolerance to frequent cold and cough, their body resistance towards diseases increased significantly and thus the occurrence of pneumonia also reduced following test drug treatment.

EXAMPLE 7

The cases receiving the organic extract of *Dioscorea bulbifera* in the dose of 200 to 250 mg per day, *Hippophae rhamnoide* in the dose of 150 to 200 mg and *Bacopa monnieri* in the dose of 200 to 250 mg exhibited improvement in overall mental performance particularly improvement in attention and memory performance. An early fatigue which was a major complaint among the subjects, improved to a great extent and a better physical fitness was reported by the subjects.

EXAMPLE 8

When the organic extract of *Dioscorea bulbifera* in the dose of 150 to 250 mg per day and *Bacopa monnieri* in the dose of 250 to 300 mg per day was administered, a significant reduction in hyper excitability, aggressive behaviour, anxiety and stress including depressive behaviour improved among the test drug treated group. A regulated improved behaviour exhibited the beneficial role of this combination.

Process of Extraction

The tuberous part of the *Dioscorea bulbifera* was properly washed and shed dried. After cutting in pieces the tuber were initially extracted with alcohol at 60 to 70 c for 70 hrs. The solvent was recovered at same temperature on single distillation set of 90% concentration. The organic extract was further separated by column chromatography method to obtain crystals. The chemical characterization of the crystal was made by HPTLC and spectroscopic method. After chemical characterization, the extracted material was subjected to experimental study for the evaluation of the therapeutic potential of the extracted materials. The total extracted material was kept between 20 to 30 C. The biological activity of the plant material can only be sustained on this temperature.

Similarly the drug fruit of dry fruits of *Hippophae rhamnoide* was initially extracted with alcohol at the temperature 60 to 70 C continuously for 70 hours. The aqueous fraction was also obtained by using buchhi vacuum rotatory apparatus at low temperature.

Shed dried total plant of the *Bacopa monnieri* was extracted in alcohol at the temperature of 60 to 70 C to obtain extract. Further extract was treated with column chromatography to obtain the crystals. The chemical characterization of crystal was done by HPTLC and spectroscopic methods.

The extract in the crystalline form was subjected to animal study for safety and efficacy profile. The whole process was performed on a particular temperature in order to obtain various chemical constituents responsible for the therapeutic efficacy. The therapeutic efficacy can only be obtained if all the chemical constituents are mixed for oral consumption.

It was found that when the organic extract of *Dioscorea bulbifera* along with the organic extract of *Hippophea rhamnoide* was given in the doses described continuously for long period the subject showed marked reduction in the level of systolic and diastolic blood pressure following cold pressure following cold pressure test. The average variation in the level of circadian blood pressure also reduced. Thus in potential hypertensive cases the early onset of Hypertension can be minimized after oral administration of this formulation. Thus the anti atherosclerotic property is proved by the oral administration of above formulation.

When the organic extract of *Dioscorea bulbifera* along with extract of dry fruits of *Hippophae rhamnoide* was given to subjects hereinabove, a mark reduction in the post prandia blood sugar level was observed. It indicates that the combined effect of *Dioscorea bulbifera* and *Hippophae rhamnoide* played a preventive role in the development of frank diabetes in the susceptible cases.

When organic extract of *Bacopa monieri* particularly different glycoside fraction along with the organic extract of *Diosscorea bulbifera* was given (Dioscorea bulbifera 150 to 300 mg, Bacopa monnieri 150 to 450 mg), a considerable improvement was noticed in the reduction of cognitive decline along with the stabilization of systolic and diastolic blood pressure. In this particular dose the drug is beneficial in the management of senile dementia.

When the extract of *Dioscorea bulbifera* 200 to 300 mg, *Hippophae rhamnoide* 250 to 350 mg, *Bacopa monnieri* 150 to 300 mg was administered only 60 percent cases reported general feeling of well being, reduction in anxiety level and reduction in cardiovascular reactivity following cold stress. About 10 percent reduction in body weight was reported among obese individuals.

When the extract of *Dioscorea bulbifera* 250-500 mg. *Hippophae rhamnoide* 300 to 500 mg, *Bacopa monnieri* 250 to 450 mg was given, the 78 percent cases reported general feeling of well being, reduction in anxiety level 72 percent cases reported reduction in cardio vascular reactivity particularly in the form of systolic and diastolic blood pressure.

A considerable improvement was noticed in the adaptation pattern against physcial and mental stress. The 15 percent reduction in total body weight was observed.

I claim:

1. A herbal preparation for management of cardiovascular and neurologic disorders, comprising organic solvent extracts of the following constituents:
   1. *Dioscorea bulbifera*
   2. *Hippophae rhanmoides*
   3. *Bacopa monnieri* and present in the range of:

| | | |
|---|---|---|
| 1. | *Dioscorea bulbifera* | 200-500 mg |
| 2. | *Hippophae rhamnoides* | 150-400 mg |
| 3. | *Bacopa monnieri* | 100-500 mg | for every 1000 mg of said preparation.

2. The herbal preparation of claim 1, wherein the organic solvent extracts are present in the range of

| | | |
|---|---|---|
| 1. | *Dioscorea bulbifera* | 200-300 mg |
| 2. | *Hippophae rhamnoides* | 250-350 mg |
| 3. | *Bacopa monnieri* | 250-500 mg | for every 1000 mg of said preparation.

3. The herbal preparation of claim 1, comprising known additives selected from the group consisting of minerals, vitamins, salt, fillers, binders and combinations thereof.

* * * * *

UNITED STATES PATENT AND TRADEMARK OFFICE
CERTIFICATE OF CORRECTION

PATENT NO. : 7,273,626 B2  Page 1 of 1
APPLICATION NO. : 10/538464
DATED : September 25, 2007
INVENTOR(S) : Dubey It is certified that error appears in the above-identified patent and that said Letters Patent is hereby corrected as shown below:

On the title page Item 12, "United States Patent
 Prasad"

should read -- United States Patent
 DUBEY --

On the title page Item 76, "Dubey Gobind Prasad"

should read -- Gobind Prasad DUBEY --

Signed and Sealed this

Twenty-fifth Day of March, 2008

JON W. DUDAS
*Director of the United States Patent and Trademark Office*